(12) United States Patent
Taguchi et al.

(10) Patent No.: US 6,396,584 B1
(45) Date of Patent: May 28, 2002

(54) PIPETTE ADAPTER, ABSORBANCE MEASURING PIPETTE, TIP, ABSORBANCE MEASURING APPARATUS, AND ABSORBANCE MEASURING

(75) Inventors: Takeshi Taguchi; Mitsuo Hiramatsu, both of Shizuoka (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 0 days.

(21) Appl. No.: 09/536,846

(22) Filed: Mar. 28, 2000

Related U.S. Application Data

(63) Continuation-in-part of application No. PCT/JP00/00244, filed on Jan. 20, 2000.

(30) Foreign Application Priority Data

Jan. 25, 1999 (JP) ............................................. 11-015971

(51) Int. Cl.[7] ................................................. G01N 21/01
(52) U.S. Cl. ...................................... 356/436; 356/246
(58) Field of Search ................................. 356/436, 440, 356/246

(56) References Cited

U.S. PATENT DOCUMENTS

| | | |
|---|---|---|
| 4,566,203 A | 1/1986 | Johnson |
| 5,125,747 A | 6/1992 | Sayegh |
| 5,125,748 A | 6/1992 | Bjornson et al. |
| 5,271,902 A * | 12/1993 | Sakka et al. ................. 422/100 |
| 5,416,879 A * | 5/1995 | Liu .............................. 385/125 |
| 5,728,527 A | 3/1998 | Singer et al. |
| 5,844,686 A | 12/1998 | Treptow et al. .............. 356/440 |
| 6,091,490 A * | 7/2000 | Stellman et al. ............ 356/300 |
| 6,104,485 A * | 8/2000 | Wang et al. ................. 356/246 |

FOREIGN PATENT DOCUMENTS

| | | |
|---|---|---|
| JP | 57-163847 | 10/1982 |
| JP | UM 4-24055 | 2/1992 |
| JP | UM 6-16852 | 3/1994 |
| JP | 7-218423 | 8/1995 |
| JP | 8-24674 | 1/1996 |
| WO | WO98/13524 | 4/1998 |
| WO | WO98/33897 | 6/1998 |

* cited by examiner

*Primary Examiner*—Richard A. Rosenberger
(74) *Attorney, Agent, or Firm*—Leydig, Voit & Mayer, Ltd.

(57) ABSTRACT

An absorbance measuring pipette includes a pipette and a pipette adapter. The pipette adapter has a pipette attachment portion for receiving the front end of the pipette and a tip attachment portion for attaching a tip and is attachable between the pipette and the tip. The pipette adapter has an inner space continuous with respective internal spaces of the pipette and tip upon attachment. The pipette adapter includes a test light introducing window for introducing a test light into the inner space from outside and a reflecting mirror for reflecting toward the sample suction port of the tip by way of an opening in the tip attachment portion the test light introduced into the inner space through the test light introducing window.

17 Claims, 11 Drawing Sheets

TO PHOTODETECTOR

PIPETTE ADAPTER, ABSORBANCE MEASURING PIPETTE, TIP, ABSORBANCE MEASURING APPARATUS, AND ABSORBANCE MEASURING

RELATED APPLICATIONS

This is a Continuation-In-Part application of International Patent Application serial No. PCT/JP00/00244 filed on Jan. 20, 2000, now pending.

BACKGROUND OF THE INVENTION

1. Field of the Invention

The present invention relates to a pipette adapter suitably usable for measuring the absorbance of a sample in the field of pharmaceutical industry and the like, an absorbance measuring pipette comprising this pipette adapter and a pipette, and a tip attachable to this pipette adapter, as well as an absorbance measuring apparatus and absorbance measuring method for measuring the absorbance of a sample by using this absorbance measuring pipette.

2. Related Background Art

In a wide range of fields such as pharmaceutical industry, food industry, chemical industry, agriculture, forestry, and fishery, samples are analyzed by measuring their absorbance for studying and developing new drugs, screening enzymes, analyzing microorganisms, and so forth. Among such analyzing methods, examples of methods for analyzing biological samples, such as nucleic acids, proteins, and the like, which are important in bio-related fields, include the following:

(1) Since biological samples as a specimen exist by only a minute amount in general, and their quantitative determination is also important, a sample is transferred to a specific cell for measuring a minute amount. The cell containing this sample is irradiated with test light. The intensity of test light transmitted through the cell and sample is detected, and the absorbance of the sample is measured according to the result of this detection. In this case, for putting the sample into the cell, a pipette 10 and a tip 30, such as those as shown in FIG. 11, are used. The tip 30 is detachably attachable to the front end of the pipette 10, and the sample is metered into the tip 30.

(2) U.S. Pat. No. 5,844,686 discloses a method using a tip having a window for introducing test light or a reflecting mirror for reflecting the test light, attaching this tip to the front end of a pipette, and measuring the absorbance of a sample while the latter is contained in the tip. This method aims at improving the recovery ratio of the sample, preventing the sample from being contaminated upon recovery, and carrying out rapid measurement of absorbance.

SUMMARY OF THE INVENTION

The inventors have found that the following problems exist in the above-mentioned conventional absorbance measuring methods. Namely:

1) In samples such as nucleic acids, proteins, and the like, subsequent reactions are often carried out after the measurement of absorbance. In such a case, it is necessary for the sample contained in the cell for absorbance measurement to be recovered after the measurement. However, the method of above-mentioned (1) is problematic in that the recovery ratio of the sample is insufficient, the sample is contaminated upon recovery, the cell is hard to wash, and so forth.

2) The method of the above-mentioned (2), on the other hand, has problems as follows. In general, for preventing the problem of contamination from occurring, the tip is used only once and is discarded without being reused. Providing such a disposable tip with the above-mentioned window or reflecting mirror is inappropriate in that the tip becomes expensive. For reusing the tip without discarding it, washing is necessary for the tip also acting as a cell. Further, since the tip has a window for introducing test light or a reflecting mirror for reflecting the test light, it is difficult for the tip to be made smaller, whereby the invention disclosed in the above-mentioned publication is not effective for a sample having a small amount (minute amount in particular).

Therefore, in order to overcome the above-mentioned problems, it is an object of the present invention to provide a pipette adapter, an absorbance measuring pipette, an absorbance measuring apparatus, and an absorbance measuring method, by which the step of recovering a sample can be omitted, the sample can be prevented from being contaminated upon recovery, no specific cell for measurement is necessary, and the absorbance of a small amount of sample can be measured by use of an inexpensive tip.

For achieving such an object, the inventors have accomplished the present invention. Namely, the pipette adapter in accordance with the present invention is one usable together with a pipette for measuring an absorbance of a sample including a specimen, attachable between the pipette and a tip adapted to contain the sample, having an inner space continuing to respective internal spaces of the pipette and tip when attached thereto, and comprising test light introducing means for introducing test light into the inner space from outside and emitting the test light toward a sample suction port of the tip.

Thus configured pipette adapter is used as being attached between the pipette and the tip. In its attached state, the respective internal spaces of the pipette adapter, pipette, and tip are continuous. By the test light introducing means, the test light is introduced into the inner space of the pipette adapter from outside and is reflected toward the sample suction port of the tip. As a consequence, the test light is transmitted through the sample contained in the tip, whereby the absorbance of the sample can be measured. As the pipette and tip, those conventionally sold and utilized can be employed. Also, a tip made of an inorganic material such as glass, stainless steel, or the like can be used.

Preferably, the test light introducing means of the pipette adapter in accordance with the present invention comprises a test light introducing window for introducing the test light into the inner space from outside and a reflecting mirror for reflecting toward the sample suction port of the tip the test light introduced into the inner space through the test light introducing window. In this case, the test light is introduced into the inner space of the pipette adapter through the test light introducing window from outside and is reflected by the reflecting mirror so as to be emitted toward the sample suction port of the tip.

Preferably, the test light introducing means comprises an optical fiber which emits, from one end thereof disposed within the inner space toward the sample suction port of the tip, the test light guided therethrough from outside. As a consequence, the test light is guided through the optical fiber from outside and is emitted toward the sample suction port of the tip from one end of the optical fiber located within the inner space of the pipette adapter. More preferably, in this case, test light collecting means, disposed near the above-mentioned one end of the optical fiber, for collecting the test light is further provided.

Also, more preferably, the test light introducing means selectively emits toward the sample suction port of the tip only a predetermined wavelength band component of the test light introduced into the inner space from outside. As a consequence, wavelength components unnecessary for absorbance measurement can be restrained from irradiating the sample, whereby the sample within the tip can be prevented from raising its temperature.

The absorbance measuring pipette in accordance with the present invention comprises the pipette adapter in accordance with the present invention and a pipette attachable to the pipette adapter. The pipette adapter and the pipette may be detachable from each other or may be used as being integral with each other. In the case where they are detachable from each other, the pipette adapter can be washed easily as necessary. When they are integral with each other, on the other hand, their handling can be improved.

It will be useful if a tip having an inserting portion, in a substantially conical or pyramidal form, for receiving the pipette adapter, and a sample container portion, in a tubular form, having an end part formed with the sample suction port is further provided. If such a tip is used for drawing in the sample by suction, and the sample is held in the sample container portion of the tip, then the reproducibility in measuring the absorbance of the sample can be enhanced. If the tubular sample container portion is made narrower and longer, then the transmission length of the test light can be enhanced even when the amount of the sample is minute.

The absorbance measuring apparatus in accordance with the present invention is an apparatus for measuring an absorbance of a sample including a specimen and comprises (1) a light source for outputting test light; (2) the absorbance measuring pipette in accordance with the present invention introducing the test light outputted from the light source into an inner space, attaching thereto a tip adapted to contain the sample, and reflecting the test light toward the sample suction port of the tip; and (3) a detection optical system for detecting the test light outputted outside from the sample suction port of the tip attached to the absorbance measuring pipette.

In thus configured absorbance measuring apparatus, the test light outputted from the light source is introduced into the inner space of the absorbance measuring pipette, reflected toward the sample suction port of the tip attached to the absorbance measuring pipette, and outputted to the outside from the sample suction port of the tip, thereby being detected by the detection optical system. By use of the result of this detection, the absorbance of the sample in the tip is measured.

Specifically, it is preferred that arithmetic means for computing the absorbance of the sample in the tip according to an intensity of the test light detected by the detection optical system in a state where the sample is contained in the tip and an intensity of the test light detected by the detection optical system in a state where the sample is not contained in the tip or in a state where a blank sample including no specimen is contained in the tip is further provided.

If the detection optical system is capable of simultaneously or substantially simultaneously detecting intensities of a plurality of components having wavelengths different from each other in the test light outputted outside from the sample suction port of the tip, then the respective absorbance values of the sample in a plurality of wavelength components can be measured substantially simultaneously.

In addition, it is preferred that the absorbance measuring apparatus in accordance with the present invention further comprise temperature adjusting means for cooling at least the tip or causing the tip to keep a constant temperature. As a consequence, the volumetric change of air within the tip, such as thermal expansion in particular, caused by the rise or change in temperature of the tip or its surroundings is suppressed. In this case, it will be further preferable if the surroundings of the tip are also cooled.

Preferably, the pipette adapter has a side wall at least a part of which is in a conical or pyramidal form, and holding means having a bored portion to which a predetermined part of the side wall of the pipette adapter in a conical or pyramidal form is adapted to fit is further provided. As a consequence, the absorbance measuring pipette can be attached and detached quite easily. Also, the absorbance measuring pipette is held stably and firmly, whereby the misalignment of optical axis in the optical path of the test light can be reduced.

The absorbance measuring method in accordance with the present invention is a method of measuring an absorbance of a sample including aspecimen, which is a method favorably carrying out absorbance measurement for the sample by using the absorbance measuring pipette in accordance with the present invention. Namely, the absorbance measuring method in accordance with the present invention comprises a step of attaching a tip adapted to contain the sample to the absorbance measuring pipette of the present invention; a step of letting the tip to contain the sample or a blank sample including no specimen; a step of introducing test light into the inner space of the absorbance measuring pipette from outside and detecting the test light outputted to the outside from the sample suction port of the tip; and a step of calculating the absorbance of the sample contained in the tip according to an intensity of the test light detected in a state where the sample is contained in the tip and an intensity of the test light detected in a state where the sample is not contained in the tip or in a state where the blank sample is contained in the tip.

In the step of detecting the test light, it is preferred that intensities of a plurality of components having wavelengths different from each other in the test light outputted to the outside from the sample suction port of the tip be detected simultaneously or substantially simultaneously. Also, in the step of detecting the test light, it is preferred that the test light be detected while at least the tip is cooled or while the temperature of the tip is held constant.

The tip in accordance with the present invention is attachable to the pipette adapter of the present invention; and has a sample container portion containing a sample including a specimen, the sample container portion having a tubular form (shaped like either a cylinder or a polygonal tube) and having substantially parallel inner walls in a cross section taken along a center axis. Such a tip can enhance the reproducibility of optical path length of the test light passing through the sample. Further, the present invention provides a tip which is attachable to the pipette adapter of the present invention and is formed from a light-shielding member capable of substantially blocking test light irradiating a sample including a specimen. If such a tip is used for measuring the absorbance of a sample, there is substantially no possibility that part of the test light irradiating the sample may pass through the tip and enter a photodetector.

DESCRIPTION OF THE PREFERRED EMBODIMENTS

Figure 1:
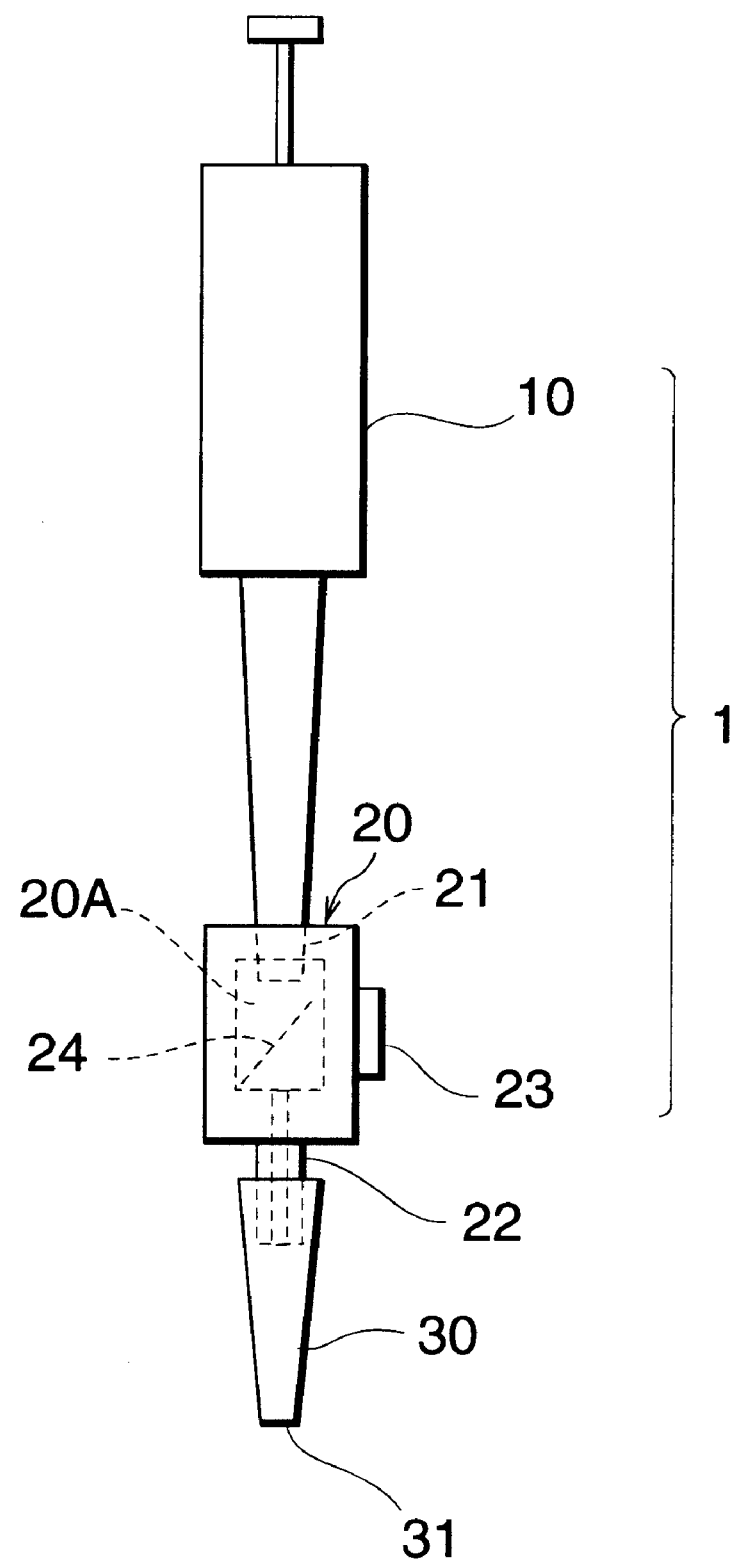
FIG. 1 is a configurational view showing a first embodiment of the absorbance measuring pipette in accordance with the present invention.

In the following, embodiments of the present invention will be explained in detail with reference to the accompanying drawings. In the explanation of drawings, constituents identical to each other will be referred to with numerals identical to each other, without their overlapping descriptions being repeated. Also, positional relationships such as upper/lower, right/left, and the like are assumed to be based on those in the drawings unless otherwise specified.

Figure 2:
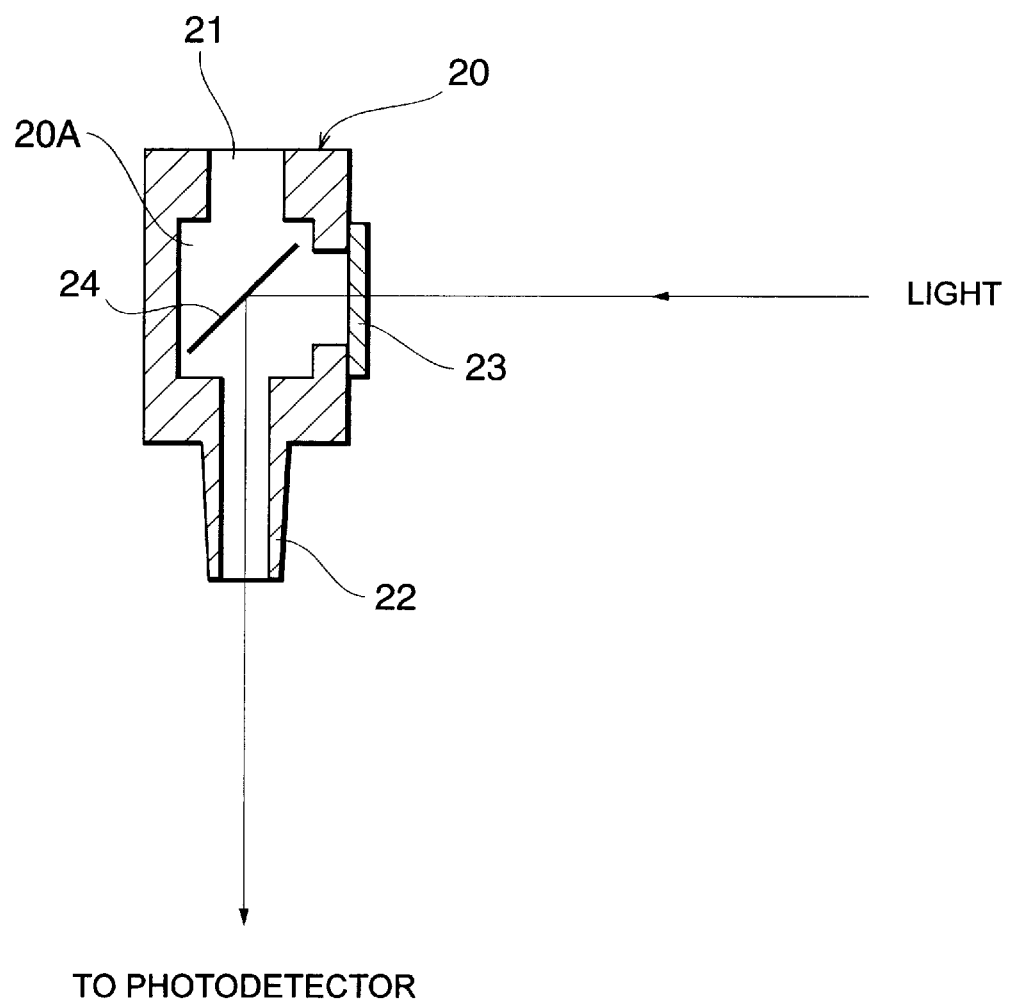
FIG. 2 is a sectional view showing the configuration of a first embodiment of the pipette adapter in accordance with the present invention.

To begin with, respective embodiments of the absorbance measuring pipette and pipette adapter in accordance with the present invention will be explained. FIG. 1 is a configurational view showing a first embodiment of the absorbance measuring pipette in accordance with the present invention. This drawing shows not only the absorbance measuring pipette 1 in accordance with this embodiment but also a tip 30. On the other hand, FIG. 2 is a sectional view showing the configuration of a first embodiment of the pipette adapter in accordance with the present invention.

Figure 11:
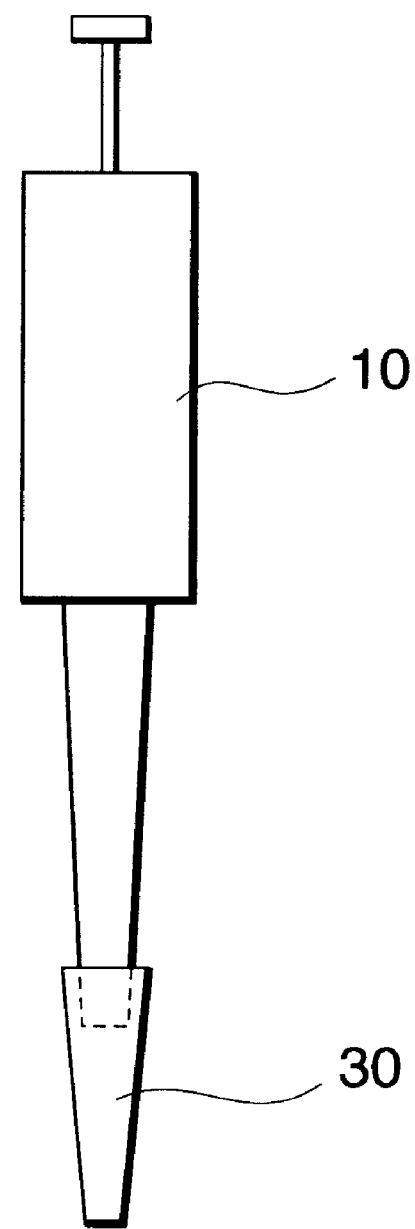
FIG. 11 is a configurational view of a conventional pipette and tip.

The absorbance measuring pipette 1 comprises a pipette 10 and a pipette adapter 20. This embodiment differs from the conventional configuration show in FIG. 11 in that the pipette adapter 20 is disposed between the pipette 10 and the tip 30. As the pipette 10 and the tip 30, those conventionally on the market and employed can be utilized. The pipette 10 and the pipette adapter 20 may be separate from each other while being freely attached to and detached from each other. If they are integral with each other, on the other hand, then their handling is easier.

The pipette adapter 20 has a pipette attachment portion 21 for receiving the front end of the pipette 10 and a tip attachment portion 22 for attaching the tip 30 thereto, and is attachable between the pipette 10 and the tip 30. The pipette adapter 20 has an inner space 20A which continues to the respective internal spaces of the pipette 10 and tip 30 upon attachment there of. Since a high hermetic property is required for both of the junction between the pipette adapter 20 and the pipette 10 and the junction between the pipette adapter 20 and the tip 30 in order to hold and stabilize a sample within the tip 30, each of the pipette attachment portion 21 and the tip attachment portion 22 is preferably coated with a material having an excellent hermetic property, for example, such as a rubber-like material or a polymer.

Also, the pipette adapter 20 comprises a test light introducing window 23 for introducing test light into the inner space 20A from outside, and a reflecting mirror 24 for reflecting toward a sample suction port 31 of the tip 30 by way of the opening of the tip attachment portion 22 the test light introduced into the inner space 20A through the test light introducing window 23. Thus, the test light introducing window 23 and the reflecting mirror 24 form test light introducing means. Here, the test light introducing window 23 may be attached to the inside instead of the outside.

Preferably, the test light introducing window 23 selectively transmits therethrough only a predetermined wavelength band component necessary for measuring the absorbance of a sample in the test light introduced into the inner space 20A from the outside. Similarly, it is preferred that the reflecting mirror 24 selectively reflect only a predetermined wavelength band component in the test light introduced into the inner space 20A. It is also preferred that the inner space 20A of the pipette adapter 20 be provided with a band-pass filter which selectively transmits therethrough only a predetermined wavelength band component of the test light introduced into the inner space 20A.

Figure 3:
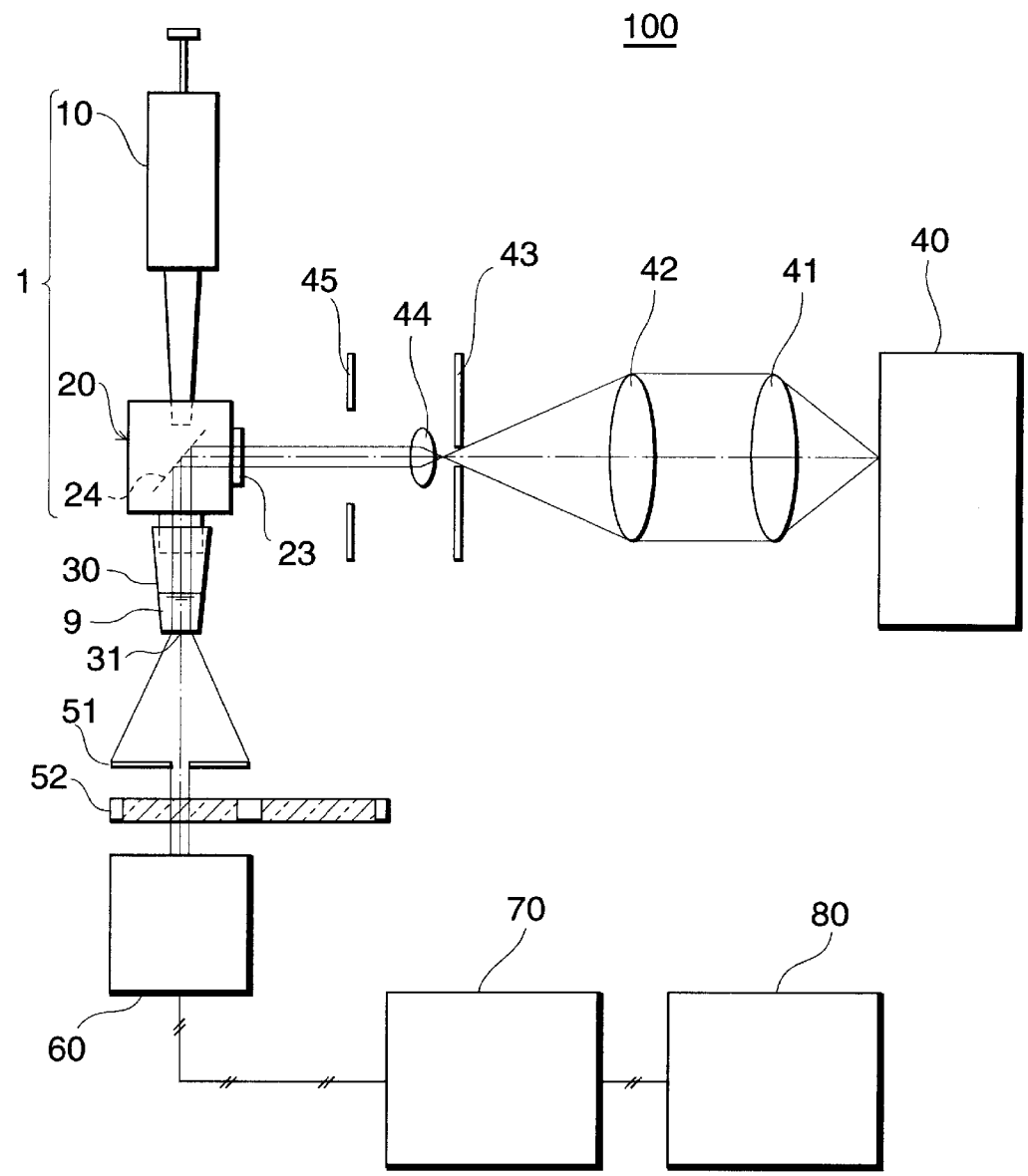
FIG. 3 is a configurational view showing a first embodiment of the absorbance measuring apparatus in accordance with the present invention.

An embodiment of the absorbance measuring apparatus in accordance with the present invention will now be explained. FIG. 3 is a configurational view showing a first embodiment of the absorbance measuring apparatus in accordance with the present invention. This absorbance measuring apparatus 100 comprises a light source 40, lenses 41, 42, an aperture 43, a lens 44, and a shutter 45 in addition to the above-mentioned absorbance measuring pipette 1. Also, the absorbance measuring apparatus 100 comprises an aperture 51, a band-pass filter 52, a photodetector 60, an ammeter 70, and a computer 80 (arithmetic means).

The irradiation optical system from the light source 40 to the shutter 45 and the detection optical system from the aperture 51 to the photodetector 60 are fixed relative to each other in terms of their positions, whereas the absorbance measuring pipette 1 is freely attached to and detached from these optical systems at a predetermined position. As an example of methods for detachably attaching the absorbance measuring pipette 1 at a predetermined position, fixing with a magnet with respect to a stationary stand housing can be noted, which is advantageous in that an appropriate optical arrangement can be realized easily.

The light source 40 outputs a predetermined wavelength band of test light for measuring the absorbance of a sample 9 contained in the tip 30, the absorbance of a blank sample (not depicted) contained therein, or the absorbance in the state where these samples are not contained therein. For example, a deuterium lamp outputting ultraviolet rays is preferably used. The shutter 45 defines the irradiation time of test light and restrains the sample 9 or blank sample from raising temperature as being irradiated with the test light for a long period of time.

The aperture 51 defines the luminous flux cross-sectional area to be determined by the photodetector 60 in the test light outputted outside from the sample suction port 31 of the tip 30. It is because of the fact that the test light outputted outside from the sample suction port 31 of the tip 30 includes not only the part directly outputted through the sample suction port 31 but also the part outputted as being reflected/scattered by the inner wall near the sample suction port 31. The aperture 51 transmits therethrough the test light mainly directly outputted through the sample suction port 31.

Further, the band-pass filter 52 selectively transmits therethrough the wavelength component to be detected by the photodetector 60 in the test light transmitted through the aperture 51. The photodetector 60 receives the test light transmitted through the band-pass filter 52 and outputs a current signal corresponding to the intensity of the test light. For example, a photomultiplier, a photodiode, or the like is preferably used.

The current signal outputted from the photodetector 60 is inputted to the ammeter 70, which then outputs a voltage signal corresponding to the current value. The voltage signal from the ammeter 70 is inputted to the computer 80. According to this voltage signal, the computer 80 determines the intensity of test light in the state where the sample 9 or the blank sample is contained in the tip 30 or in the state where none of these samples is contained therein, and calculates the absorbance of the sample based on the test light.

Without being restricted in particular, the specimen may be in the form of solution, semisolid, or solid, as long as it can be used as a sample when yielding a concentration capable of absorbance measurement with an appropriate solvent. Specific examples thereof include urine samples, blood samples, body fluid samples, and extracts from biological tissues, nucleic acids, proteins, bases, and the like as biological samples. Specimens other than biological samples include environmental samples such as river water, lake water, sea water, tap water, rainwater, incinerated ashes, wastes, or animal and plant samples in environments; generally employed metals, ceramics, plastics, their extracts or solutions, gases or their absorption products, or the like; or analysis samples such as synthesized materials and the like.

As samples for absorbance measurement, those in which the above-mentioned specimens as a solute are dissolved or dispersed in an appropriate solvent can be used. In the present invention, "blank sample" refers to a solvent (e.g., distilled water, highly pure water, or the like) containing no specimen as a solute, or a solution (e.g., buffer solution, reaction liquid including no substrate, or the like) other than the solvent.

With reference to FIG. 3, the absorbance measuring method in accordance with this embodiment will be explained together with operations of the absorbance measuring apparatus 100 in accordance with this embodiment. First, the tip 30 is attached to the absorbance measuring pipette 1, and a sample is metered and put into the tip 30 from a sample container. Subsequently, while this state is maintained, the absorbance measuring pipette 1 is attached to the absorbance measuring apparatus 100 at a predetermined position thereof. Then, the shutter 45 is opened, whereby the test light outputted from the light source 40 is focused by the lenses 41, 42, so as to pass through the aperture 43, and then is turned into parallel light by the lens 44, so as to pass through the shutter 45 and enter the test light introducing window 23 of the pipette adapter 20.

This test light is transmitted through the test light introducing window 23, so as to be introduced into the inner space 20A of the pipette adapter 20, and is reflected by the reflecting mirror 24. While being partly absorbed by the sample 9 contained in the tip 30, the reflected test light is transmitted through the tip 30 and outputted outside from the sample suction port 31 thereof.

Of the test light outputted from the sample suction port 31, a part of its luminous flux passes through the aperture 51, whereby the wavelength component to be detected is transmitted through the band-pass filter 52 and received by the photodetector 60. Then, the current signal corresponding to the light quantity (intensity) of thus received test light is outputted from the photodetector 60, and is converted into a voltage signal by the ammeter 70. This voltage signal is fed into the computer 80, and the test light intensity (hereinafter referred to as "actually measured sample value") corresponding to this voltage signal is determined.

Here, an average optical path length (hereinafter referred to as "sample optical path length") is determined from the amount of the sample 9 contained in the tip 30. Specific methods of calculating the optical path length are not restricted in particular. It may be visually measured by use of a separately provided scale or the like, the tip 30 may be provided with a scale corresponding to the optical path length, or the pipette 10 may display the optical path length.

Also, the optical path length can be determined from the kind and form of the employed tip and the amount of sample. Storing their relationship into the computer 80 beforehand is convenient in that the optical path length can easily be determined therefrom. Here, it is also preferred that an optical path length correction factor in which influences of scattered light or reflected light in the tip 30 are theoretically or experimentally (empirically) evaluated is calculated beforehand.

Before or after measuring the absorbance of the sample 9, on the other hand, the tip 30 is replaced, and a test light intensity (hereinafter referred to as "reference value") is determined, as with the absorbance measurement of the sample 9, while the blank sample is contained in the tip 30 in place of the sample 9 or while nothing is contained in the tip 30. In the case where the blank sample is used, an optical path length (hereinafter referred to as "reference optical path length") is determined as with the sample optical path length. Then, according to the actually measured sample value, reference value, sample optical path length, and reference optical path length, and the optical path length correction factor if necessary, the computer 80 calculates the absorbance of the sample 9. Further, in order to be quantitatively determined from the absorbance, the specimen concentration in the sample 9 can be calculated from the above-mentioned optical path lengths and the molar absorption coefficient of the specimen.

The pipette adapter 20, the absorbance measuring pipette 1 equipped with this pipette adapter 20, and the absorbance measuring apparatus 100 equipped with this absorbance measuring pipette 1 in accordance with the present invention as explained in the foregoing make it easier to transfer the sample 9 having completed the absorbance measurement to a reaction container, for example, and subject thus transferred sample 9 to various aimed reactions subsequent to the absorbance measurement. Hence, the step of recovering the sample can be omitted, whereby the sample can be prevented from being contaminated upon recovery.

Also, a conventional expensive cell for absorbance measurement is unnecessary, and the absorbance of a small amount of sample can be measured quickly. Further, the measurement is inexpensive since a conventional commercially available tip 30 can be used. Also, the tip 30 can be made smaller, whereby it is quite useful for measuring a very small amount of sample. In addition, in the case where the tip 30 has to be discarded depending on the kind of the sample 9 after being used, it is possible to suppress the cost therefor and reduce the amount of waste, since the tip 30 is inexpensive and small.

Further, since the test light can be emitted toward the sample suction port 31 of the tip 30 by use of the reflecting mirror 24, the absorbance of the sample 9 contained in the tip 30 can be measured in this state. Therefore, it is advantageous in that the apparatus configuration can be simplified. Furthermore, since the wavelength component to be detected can be selected by the band-pass filter 52, and the photodetector 60 can detect this component alone, background light can be reduced greatly. Hence, the sensitivity in measurement of absorbance can be improved.

Moreover, since the test light introducing window 23 and/or the reflecting mirror 24 can transmit or reflect the wavelength band component of light necessary for measuring the absorbance of the sample 9, the latter can be restrained from being irradiated with wavelength components unnecessary for absorbance measurement. Therefore, the rise in temperature of the sample 9 in the tip 30 can be prevented. As a consequence, the changes in optical path length and refractive index caused by volumetric expansion of the sample 9 can be suppressed, whereby the accuracy in absorbance measurement can fully be prevented from decreasing. Also, the thermal expansion of the air within the tip 30 is suppressed, whereby the sample 9 can fully be kept from leaking out from the tip 30 because thereof.

Figure 4:
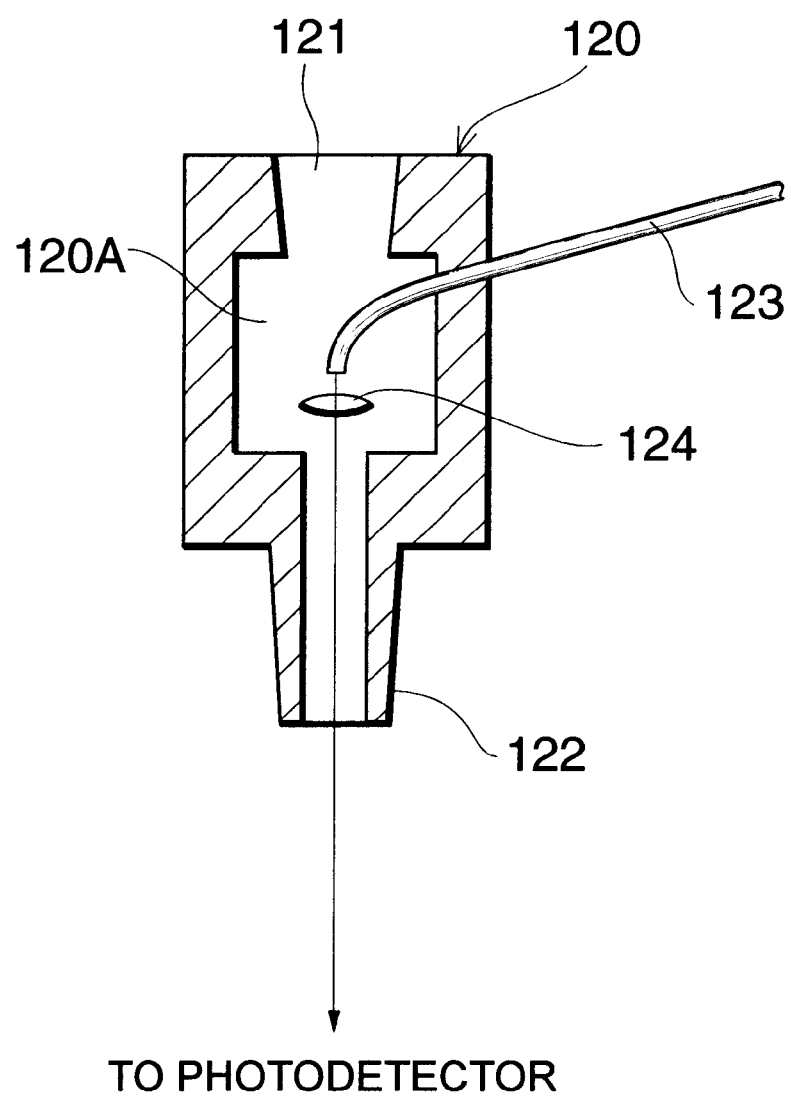
FIG. 4 is a sectional view showing the configuration of a second embodiment of the pipette adapter in accordance with the present invention.

Another embodiment of the pipette adapter in accordance with the present invention will now be explained. FIG. 4 is a sectional view showing the configuration of a second embodiment of the pipette adapter in accordance with the present invention. This pipette adapter 120 has a pipette attachment portion for receiving the front end of a pipette 10 and a tip attachment portion 122 for attaching a tip 30 thereto, and is attachable between the pipette 10 and the tip 30. The pipette adapter 120 also has an inner space 120A which continues to the respective internal spaces of the pipette 10 and tip 30 upon attachment thereof.

Since a high hermetic property is required for both of the junction between the pipette adapter 120 and the pipette 10 and the junction between the pipette adapter 120 and the tip 30 in order to hold and stabilize the sample within the tip 30, each of the pipette attachment portion 121 and the tip attachment portion 122 is preferably coated with a material having an excellent hermetic property, for example, such as a rubber-like material or a polymer.

Also, the pipette adapter 120 comprises an optical fiber 123 (test light introducing means) and a lens 124 (test light collecting means). The optical fiber 123 outputs, from one end thereof disposed in the inner space 120A, the test light guided therethrough from the outside. The lens 124 turns the test light outputted from the above-mentioned one end of the optical fiber 123 into parallel light, and emits this test light toward the sample suction port 31 of the tip 30 through the opening of the tip attachment portion 122.

Further, it is preferred that the inner space 120A of the pipette adapter 120 be provided with a band-pass filter which selectively transmits therethrough only a predetermined wavelength band component of the test light introduced in the inner space 120A. As the optical fiber 123, one having a front end shaped into a spherical lens or SELFOC lens is also preferably used. In this case, the lens 124 is unnecessary, and the front end portion of the optical fiber 123 also acts as the test light collecting means.

When such a pipette adapter 120 is employed, the test light outputted from a light source 40 is inputted to the optical fiber 123 from the outer end thereof, guided through the optical fiber 123, and emitted from the inner end of the optical fiber 123 within the inner space 120A. Thus emitted test light passes through the sample 9 within the tip 30 in a manner similar to that mentioned above.

Thus configured pipette adapter 120 irradiates the sample 9 contained in the tip 30 with the test light by using the optical fiber 123, as with the pipette adapter 20 shown in FIG. 3 having the reflecting mirror 24. Therefore, the apparatus configuration can be simplified.

Also, the lens 124 or the lens function provided in the front end portion of the optical fiber 123 irradiates the sample 9 with the focused test light. Hence, it is not necessary to use the lenses 41, 42, 44 shown in FIG. 3, whereby the apparatus configuration can be made simpler. Further, the light source 40 shown in FIG. 3 can be disposed at a position distanced from the tip 30, whereby the air within the tip 30 and the sample 9 can be restrained from raising temperature due to the radiant heat of the light source 40 or the thermal conduction from the light source 40. As a result, the sample 9 can be kept from leaking out from the tip 30 and from expanding its volume.

Figure 5:
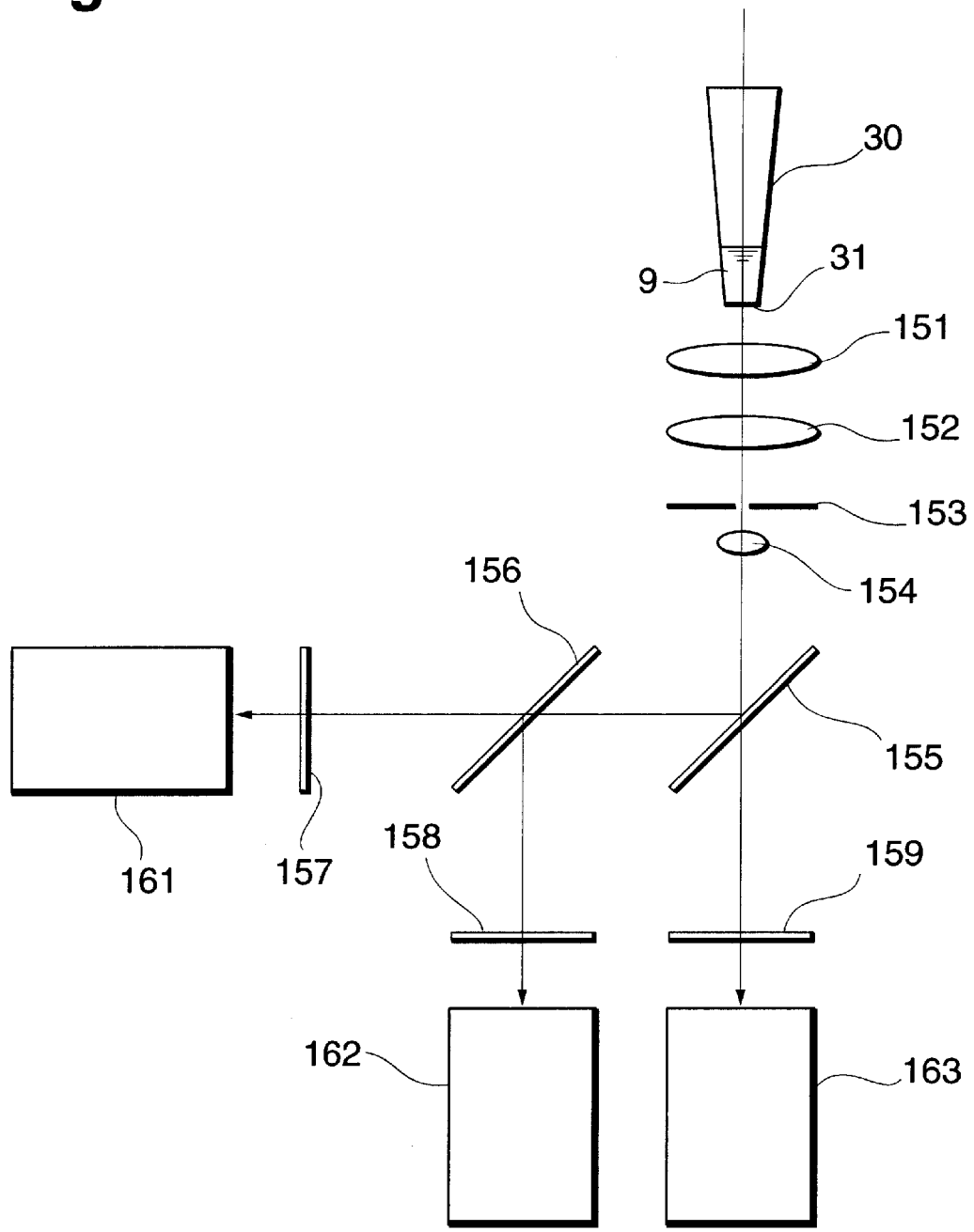
FIG. 5 is a configurational view showing another embodiment concerning the detection optical system in the absorbance measuring apparatus in accordance with the present invention.

Another embodiment of the detection optical system in the absorbance measuring apparatus will now be explained. FIG. 5 is a configurational view of an embodiment concerning the detection optical system in the absorbance measuring apparatus in accordance with the present invention. This detection optical system comprises, successively from the tip 30, lenses 151, 152, an aperture 153, a lens 154, dichroic mirrors 155, 156, band-pass filters 157 to 159, and photomultipliers (photodetectors) 161 to 163. In the following, assuming that the sample 9 to be subjected to absorbance measurement within the tip 30 contains a nucleic acid or protein as a specimen, a case where three wavelength components consisting of measurement light components at 260 nm and 280 nm and a reference light component at 320 nm are simultaneously detected will be explained.

The dichroic mirror 155 selectively reflects components in the wavelength band of 250 to 300 nm, while transmitting therethrough the other wavelength components. The dichroic mirror 156, on the other hand, selectively reflects components in the wavelength band of 250 to 270 nm, while transmitting therethrough the other wavelength components. The band-pass filters 157, 158, and 159 have their respective maximum transmission wavelengths at 280 nm, 260 nm, and 320 nm.

In this detection optical system, the test light transmitted through the tip 30 while being partly absorbed by the sample therein and then outputted to the outside from the sample suction port 31 is once focused by the lenses 151, 152, passes through the aperture 153, and then is turned into parallel light by the lens 154. The test light thus turned into parallel light is separated into three wavelength components by the dichroic mirrors 155 and 156 and the band-pass filters 157 to 159.

Namely, the 280 nm wavelength component is reflected by the dichroic mirror 155, passes through the dichroic mirror 156 and the band-pass filter 157, and then is detected by the photomultiplier 161. The 260 nm wavelength component is reflected by the dichroic mirror 155 and also by the dichroic mirror 156, passes through the band-pass filter 158, and then is detected by the photomultiplier 162. The 320 nm wavelength component passes through the dichroic mirror 155 and the band-pass filter 159, and then is detected by the photomultiplier 163.

Such a detection optical system can simultaneously detect the three wavelength components (at wavelengths of 280 nm, 260 nm, and 320 nm). In general, though depending on the viscosity thereof, the solution drawn into the tip by suction is hard to achieve a completely still state, and its state usually changes with time and sometimes delicately on a second-by-second basis. Such a change may be so minute that it hardly influences the absorbance measurement; or may cause a refractive index change to such an extent that, depending on temperature fluctuations, vibrations, airflow, or the like in measurement environments, the intensity of the test light incident on the photodetector significantly fluctuates. Under such circumstances, the above-mentioned detection optical system can simultaneously detect a plurality of wavelength components of test light, whereby errors in measured absorbance value caused by changes in state of the sample 9 can be lowered.

Figure 6:
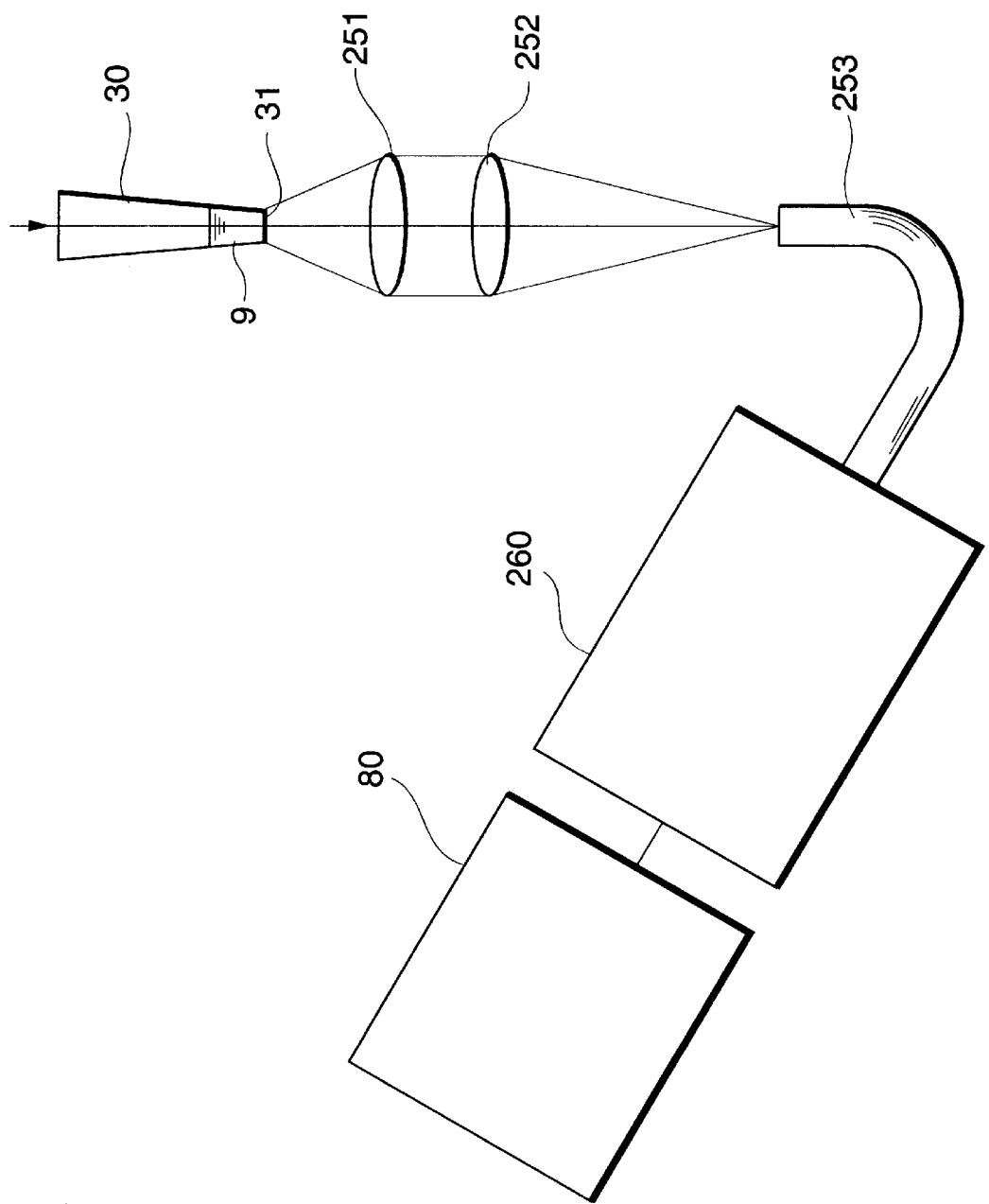
FIG. 6 is a configurational view showing still another embodiment concerning the detection optical system in the absorbance measuring apparatus in accordance with the present invention.

Still another embodiment of the detection optical system in the absorbance measuring apparatus will now be explained. FIG. 6 is a configurational view of an embodiment concerning the detection optical system in the absorbance measuring apparatus in accordance with the present invention. This detection optical system comprises, successively from the tip 30, lenses 251, 252, an optical fiber 253, and a spectrometer 260.

In this detection optical system, the test light partly absorbed by the sample 9 in the tip 30 and then outputted outside from the sample suction port 31 is collected by the lenses 251, 252, inputted to one end of the optical fiber 253, guided through the optical fiber 253, and then outputted from the other end thereof so as to be inputted to the spectrometer 260. Then, the test light is spectrally resolved by the spectrometer 260, and a spectrum of the test light is detected thereby. As a consequence, a spectrum of the test light in a predetermined wavelength band is detected, and spectral analysis is carried out by the computer 80 according to a typical method.

Such a detection optical system can determine intensities of given wavelengths of test light components in a predetermined wavelength band nearly at the same time (substantially at the same time). Also, a single detection optical system can deal with individual samples 9 including respective specimens having absorption spectra different from each other. Hence, versatility can be enhanced in the absorbance measurement for the samples 9, whereby the labor of rearranging band-pass filters and the like can be omitted.

Also, if the wavelength resolution of the spectrometer is enhanced, then differences in absorption spectrum forms resulting from differences in molecular structure of specimen materials, such as differences in molecular skeletons and in functional groups, for example, can be detected, whereby the purity of the specimen can be detected at the same time with the absorbance measurement for the sample 9. In this case, it is further preferred that the spectrometer 260 be equipped with a photodetector having a high quantum efficiency for the wavelength region to be detected and a spectral characteristic with a less wavelength dependency (a nearly flat spectral sensitivity curve).

Figure 7:
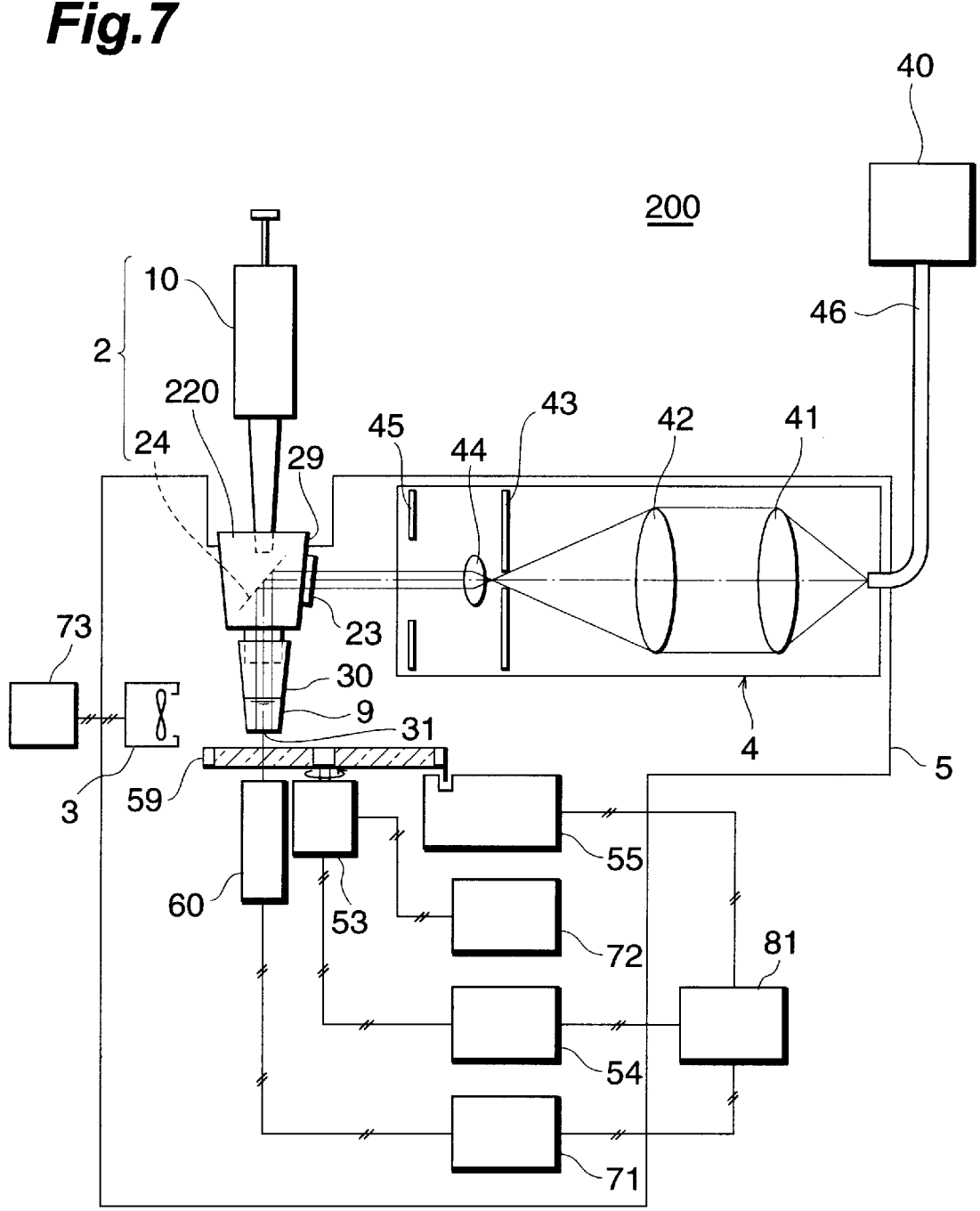
FIG. 7 is a configurational view showing a second embodiment of the absorbance measuring apparatus in accordance with the present invention.
Figure 8:
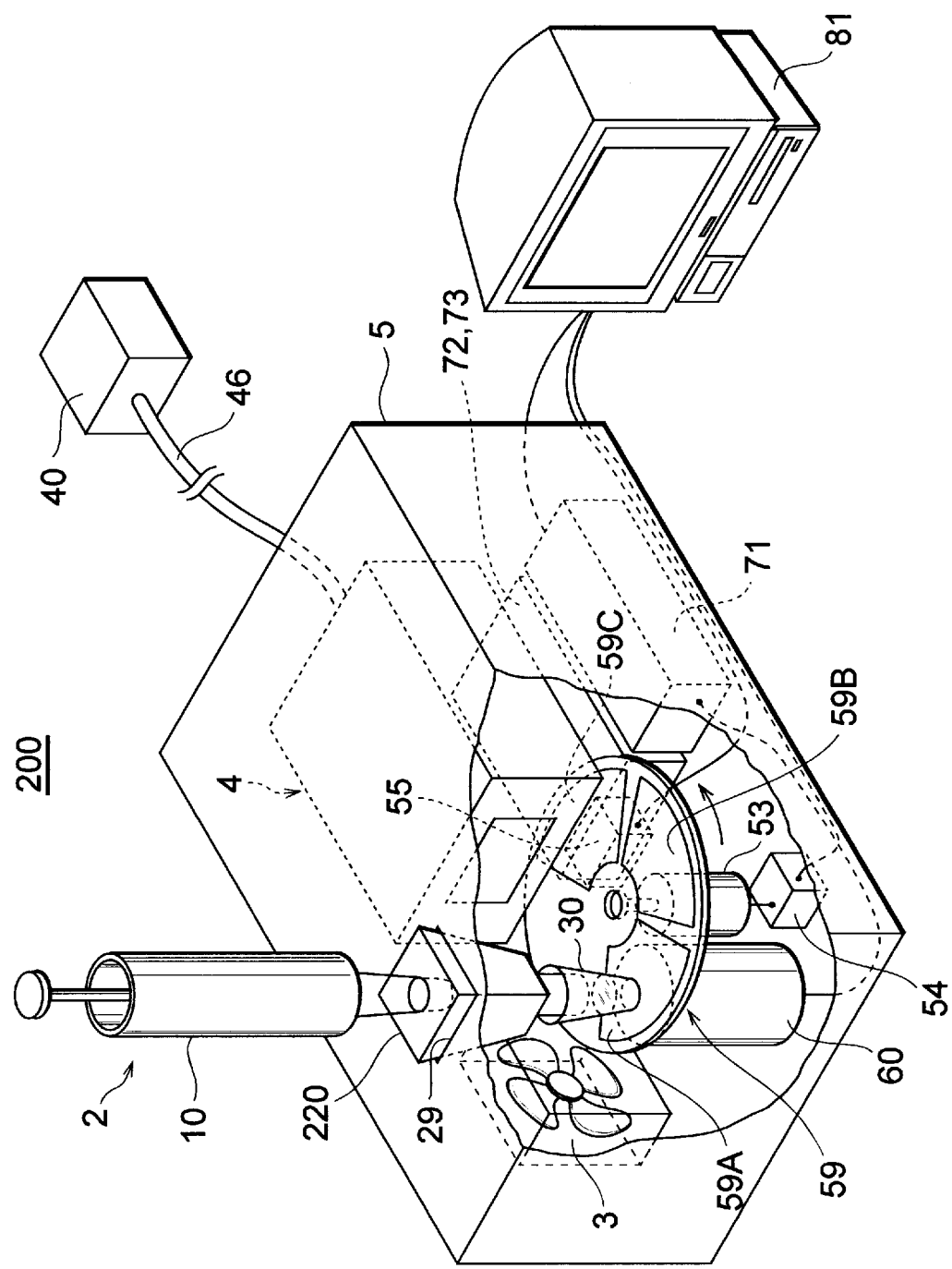
FIG. 8 is a perspective view showing the second embodiment of the absorbance measuring apparatus in accordance with the present invention.

Another embodiment of the absorbance measuring apparatus in accordance with the present invention will now be explained. FIG. 7 is a configurational view showing a second embodiment of the absorbance measuring apparatus in accordance with the present invention, whereas FIG. 8 is a perspective view thereof. The absorbance measuring apparatus 200 comprises an absorbance measuring pipette 2 constituted by a pipette 10 and a pipette adapter 220 whose side walls are shaped like a pyramid.

In this absorbance measuring pipette 2, the pipette adapter 220 is secured to an attachment hole 29 (bored portion) of a housing 5 (holding means). The opening area of the attachment hole 29 is greater than the minimum value of the horizontal cross-sectional area of the pipette adapter 220 but smaller than the maximum value thereof, and the pipette adapter 220 fits in the attachment hole 29, whereby the absorbance measuring pipette 2 is firmly secured.

Disposed within the housing 5 are an optical system 4, a cooling fan 3, a filter disk 59, a rotating motor 53, a rotating motor controller 54, a transistor-transistor logic (TTL) signal generator circuit 55 in synchronization with the number of revolutions of the filter disk 59, a photodetector 60, a current-to-voltage converter 71, and power supplies 72, 73. The optical system 4 is constituted by the lenses 41, 42, aperture 43, lens 44, and shutter 45 shown in FIG. 3, whereas a light source 40 disposed outside the housing 5 is optically coupled to the optical system 4 by way of an optical fiber 46, and these members constitute an irradiation optical system.

The cooling fan 3 (temperature adjusting means) is used for blowing air to the tip 30 attached to the pipette adapter 220 and its surroundings, and is connected to the power supply 73. The filter disk 59 is constituted by a disk having three kinds of band-pass filters 59A, 59B, and 59C as shown in FIG. 8, whereas the rotary shaft of the rotating motor 53 connected to the power supply 72 is coaxially secured thereto. As the band-pass filters 59A, 59B, and 59C, those having respective maximum transmission wavelengths of 260 nm, 280 nm, and 320 nm are employed, for example, while they have the same shape and area. Thus, the filter disk 59 and the photodetector 60 constitute a detection optical system.

Also, the tip 30, the filter disk 59, and the photodetector 60 are arranged such that they are disposed closer to each other as compared with their equivalents in the absorbance measuring apparatus 100 shown in FIG. 3, while the distances between the tip 30 and the individual band-pass filters 59A, 59B, 59C are identical to each other. By way of the current-to-voltage converter 71, the photodetector 60 is connected to a computer 81 (arithmetic means) equipped with both of an analog-to-digital (AD) converter and an interface. The computer 81 calculates the absorbance of the sample 9 by using the intensity of the current signal of the test light detected by the photodetector 60 or the like, reads out the TTL signal in synchronization with the number of revolutions of the filter disk 59, and further controls the rotation of the filter disk 59 by way of the rotating motor controller 54.

The current-to-voltage converter 71 has a characteristic satisfying an input signal condition by which the computer 81 can operate normally. It may further comprise an amplifying function under some circumstances. Depending on the kind of photodetector 60, the ammeter 70 shown in FIG. 3 may be used in place of the current-to-voltage converter 71.

Operations of the absorbance measuring apparatus 200 in accordance with this embodiment will now be explained with reference to FIGS. 7 and 8. First, power switches including those for the light source 40 and cooling fan 3 are turned on. The air blown from the cooling fan 3 suppresses the temperature rise in the tip 30 and sample 9 caused by the irradiation with test light or by the heat radiated or conducted from heat sources, or cools the tip 30 and sample 9. Also, it will be further preferable if a sufficient warm-up operation is carried out before the actual measurement. Subsequently, the tip 30 is attached to the absorbance measuring pipette 2, and a blank measurement liquid which is a solution containing only a solvent without the sample is metered into the tip 30. This absorbance measuring pipette 2 is inserted into the attachment hole 29 of the housing 5 from there above, and secured to the housing 5.

Further, the rotating motor 53 rotates the filter disk at a predetermined frequency of rotation, e.g., 10 Hz. In this state, the shutter 45 of the optical system 4 is opened, whereby the test light outputted from the light source 40 passes through the test light introducing window 23 of the pipette adapter 220 and irradiates the sample 9 by way of the reflecting mirror 24 within the pipette adapter 220.

The test light transmitted through the blank measurement liquid is emitted from the sample suction port 31 of the tip 30 toward the filter disk 59. The filter disk 59 is rotating as mentioned above, so that the test light having a predetermined wavelength enters the photodetector 60 while each band-pass filter 59A, 59B, 59C passes under the sample suction port 31 of the tip 30, whereby a current signal corresponding to each wavelength component is outputted. While the plate portion of the filter disk 59 not provided with the band-pass filters 59A, 59B, 59C passes under the sample suction port 31, the test light is blocked thereby, whereby dark current is outputted from the photodetector 60.

The current signal corresponding to each wavelength component and the dark current are converted into voltages by the current-to-voltage converter 71, and these output values are read out by the computer 81 at timings of TTL signals in synchronization with the filter disk 59 and are stored into the computer 81. In the case where the frequency of rotation is 10 Hz, one revolution of the filter disk 59 takes only 0.1 second, whereby it can be assumed that the individual wavelength components are detected at substantially the same time.

Subsequently, with the sample 9 replacing the blank measurement liquid, the above-mentioned measurement is repeated. A correction for subtracting a data value corresponding to dark current from the respective data values corresponding to the band-pass filters 59A, 59B, 59C is carried out, and the absorbance of each wavelength component by the sample 9 is calculated from thus obtained current signal of each wavelength component and the data value of the blank measurement liquid previously stored in the computer 81. Also, if necessary, the absorbance in the case where the above-mentioned optical path length correction is effected can be calculated. The absorbance may also be calculated as being corrected by a measured value obtained through a predetermined band-pass filter transmitting therethrough only light having a wavelength which is not absorbed by the sample 9.

In thus configured absorbance measuring apparatus 200, since the side walls of the pipette adapter 220 have a pyramidal form, and the pipette 2 is secured to the housing 5 having the attachment hole 29 to which a predetermined part of the side walls fits and attaches, attachment and detachment are quite easy. Also, vibrations upon attachment are suppressed, whereby the sample 9 can be prevented from leaking out from the tip 30 due to vibrations.

Further, since the absorbance measuring pipette 2 is held stably and firmly, the reproducibility of attaching positions is high, and the misalignment of the optical axis in the optical path of the test light is reduced. Hence, the accuracy and precision in absorbance measurement can be improved. In this case, if dimensional accuracy is enhanced in the side walls of the pipette adapter 220 and the attachment hole 29 of the housing 5, the reproducibility of attaching positions will further improve. Furthermore, since individual wavelength components of test light can be detected nearly at the same time (substantially at the same time), errors in measured absorbance values due to changes in the state of the sample 9 can be reduced as in the effects of the above-mentioned detection optical system shown in FIG. 5.

Also, while the pipette adapter is desired to be made of a highly hermetic material, as a result, the air within the pipette adapter and tip may thermally expand when their temperature rises upon heating, thereby pushing out the sample from within the tip. In the absorbance measuring apparatus 200 of this embodiment, though there is a possibility of the rise in measurement ambient temperature (room temperature) and the rotating motor 53 becoming a heat source, the cooling fan 3 cools and/or holds the temperature of the tip 30 and its surroundings, thereby significantly suppressing the expansion of air within the tip 30 and pipette adapter 220. Hence, the sample 9 can favorably be kept from leaking out from the tip 30. Also, since the sample 9 itself is forcibly cooled, the heating of the sample 9 upon irradiation with test light is suppressed, whereby the sample 9 can further be prevented from leaking out from the tip 30.

Further, since the light source 40 is located outside the housing 5, the pipette adapter 220 and the tip 30 are fully prevented from raising temperature due to the radiation heat of the light source 40. Also, even when the housing 5 is heated by the radiation heat of the light source 40, and the pipette adapter 220 and the tip 30 raise temperature due to the heat conduction from the housing 5, changes in temperature of the sample 9 in the tip 30 can be suppressed. Therefore, the leakage from the tip 30 can further be prevented from occurring.

Further, while the test light is refracted when transmitted through the sample 9 and is emitted from the front end of the tip 30 (sample suction port 31) at various emission angles, the tip 30 and the filter disk 59 are disposed close to each other, and the filter disk 59 and the photodetector 60 are disposed close to each other, whereby substantially the whole test light emitted from the tip 30 can be made incident on the photodetector 60. Therefore, the detection efficiency (geometric efficiency) of test light by the photodetector 60 is enhanced, whereby absorbance measurement with a higher sensitivity is possible.

Figure 9:
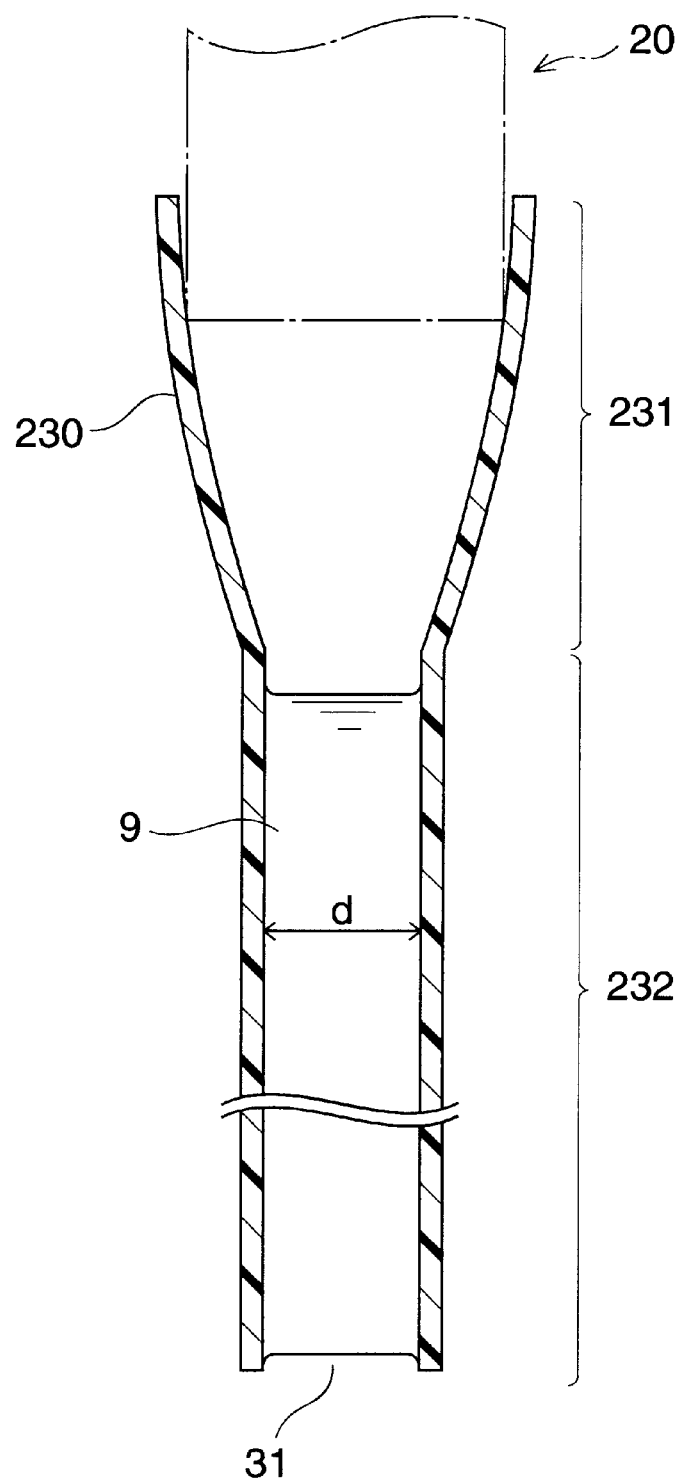
FIG. 9 is a sectional view showing the tip provided in another embodiment of the absorbance measuring pipette in accordance with the present invention.

Another embodiment of the absorbance measuring pipette will now be explained. FIG. 9 is a sectional view showing the tip provided in this embodiment of the absorbance measuring pipette in accordance with the present invention. This absorbance measuring pipette is constituted by the pipette adapter 20 for the absorbance measuring pipette 1 shown in FIG. 1, and a tip 230 shown in FIG. 9 detachably attached thereto.

This tip 230 has a conical attachment portion 231 (inserting portion) for letting a tubular end portion of the pipette adapter 20 to be inserted into the inside thereof so as to be attached thereto, and a sample container portion 232 in a tubular form provided with a sample suction port 31; whereas the sample container portion 232 has an internal diameter d smaller than that of the end portion of the pipette adapter 20. In this absorbance measuring pipette, a sample 9 is contained in the sample container portion 232, and the absorbance of the sample 9 is measured while this state is held. The length (depicted height) of the sample container portion 232 is not restricted in particular, and it is preferred that the uniformity of the inside diameter d (degree of parallelism of the inside) be kept favorably.

The absorbance measuring pipette having such a tip 230 can enhance the reproducibility of optical path length of the test light passing through the sample 9. Therefore, the accuracy and precision in absorbance measurement can be improved. If the tubular sample container portion 232 is made narrower and longer, then the transmission length of test light can be enhanced even when the amount of the sample is very small, whereby absorbance measurement with a higher sensitivity becomes possible. It is desirable that the inner face of the tip 230 be highly hydrophobic in order for the sample 9 to run smoothly. Here, making the inside diameter d of the sample container portion 232 smaller is preferable since it can prevent the sample 9 from leaking out.

Preferably, the tip 230 is formed from a light-shielding member which can substantially block the test light, i.e., a light-shielding member which does not substantially transmit the test light therethrough. An example of the tip 230 made of such a member is a tip made of black polypropylene. Such a tip which does not substantially transmit the test light therethrough is quite effective, in particular, in the case where the sample container portion 232 of the tip 230 has such a small inside diameter that a part of the test light may pass through the tip 230 and enter the photodetector.

For securing the absorbance measuring pipette 1, 2, it will be sufficient if the pipette is held as perpendicular as possible and such that the sample 9 can be drawn into the tip 30, 230 by the same or substantially the same suction force. Without being restricted to the above-mentioned method by means of a magnet and the attachment to the housing 5, a jig such as a typical pipette stand or the like may also be used, for example. Also, when drawing the sample 9 into the tip 30, 230 by suction, the rate of reducing the pressure and the negative pressure may be made identical or substantially identical at each time.

Further, it will be sufficient if at least a part of the side walls of the pipette adapter 220 is in a conical or pyramidal form. For example, it will be sufficient if one face of the side walls has a tapered portion. Furthermore, the side walls of the pipette adapter 220 may be shaped not only like a quadrangular pyramid, but also like a triangular pyramid or a pentagonal or higher pyramid, or like a circular cone (requiring means for positioning the test light introducing window 23 in this case). Also, in place of or in addition to the cooling fan 3, a cooling device (temperature adjusting means) such as a Peltier device or the like may be disposed at the attachment hole 29 and/or side walls of the pipette adapter 220 in the absorbance measuring apparatus 200.

Further, the light source 40, rotating motor 53, and the like, which can become a heat source, may be provided with a cooling fan. In this case, in the absorbance measuring apparatus 200, the light source 40 may be disposed within the housing 5, and it is preferred that the pipette adapter 220 be cooled aggressively if it is made of a material having a high thermal conductivity. The filter disk 59 may also have two kinds of band-pass filters or four or more kinds of band-pass filters. If a wavelength-variable laser is employed as the light source 40, then an absorption spectrum can be obtained without using the spectrometer 260.

Though the foregoing embodiments relate to manual pipettes, the present invention is also applicable to automatic pipettes such as high-throughput screening apparatus. Automatic pipettes are not only excellent in the reproducibility of suction of samples, but also have a characteristic that their optical systems have a high reproducibility. Hence, if the present invention is applied to an automatic pipette, then an apparatus system quite suitable for measuring the absorbance of a small amount of sample can be constructed.

Figure 10:
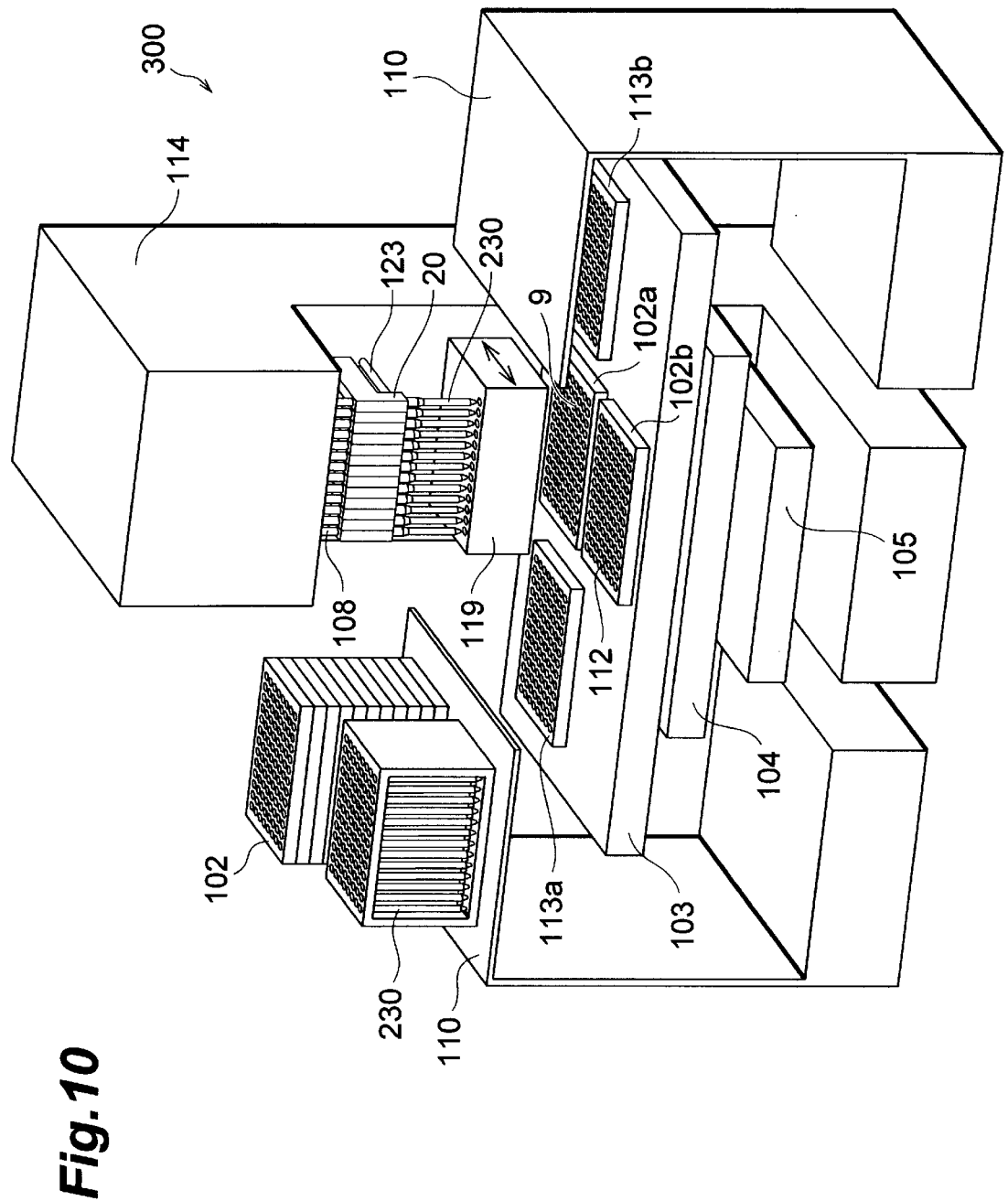
FIG. 10 is a perspective view showing a third embodiment of the absorbance measuring apparatus in accordance with the present invention.

An example of the apparatus using such an automatic pipette will now be explained. FIG. 10 is a perspective view showing a third embodiment of the absorbance measuring apparatus in accordance with the present invention. A screening apparatus 300 (absorbance measuring apparatus) comprises a plurality of pipette adapters 20 arranged in parallel in its main body 114, and a detection optical system 119 disposed under the pipette adapters 20. This detection optical system 119 has photodetectors whose number corresponds to that of the pipette adapters 20 and is movable (back and forth in the drawing) in directions perpendicular to the optical axis of the test light. Here, the pipette adapters 20 may be movable, and the detection optical system 119 may be either stationary or movable in this case. Also, a single pipette adapter 20 may be used.

Disposed under the detection optical system 119 are X-, Y-, and Z-stages 103, 104, 105, by which equipment such as a microplate mounted on the X-stage 103 is moved three-dimensionally. Here, the pipette adapters 20 may be three-dimensionally movable, and it will be sufficient if one stage for mounting equipment such as a microplate is provided in this case. Further, holding tables 110 for placing equipment are disposed above side portions of the X-stage 103.

An example of procedures for absorbance measurement (screening) carried out by the screening apparatus 300 is as follows:

(1) First, tips 230 and microplates 102 are set at predetermined positions of a holding table 110.

(2) Microplates 102a, 102b containing a sample 9 including a specimen and a reference sample (a sample with a known absorbance or a blank sample) 112, respectively, are disposed at the center part of the X-stage 103.

(3) The X-, Y-, and Z-stages 103, 104, 105 are driven, such that the tips 230 are taken onto the X-stage 103 from the holding table 110 and then are moved to positions directly under their corresponding pipette adapters 20.

(4) The Z-stage 105 is driven so as to move up and down, so that a plurality of tips 230 are attached to their respective pipette adapters 20 at once.

(5) The X- and Y-stages 103, 104 are driven so as to move the microplate 102b containing the reference sample 112 to a position directly under the tips 230.

(6) The Z-stage 105 is driven so as to move up and down, so that the front end portions of the tips 230 are inserted into the reference sample 112 in the microplate 102b.

(7) An injection unit (not depicted; connected to pipes 108) incorporated in the main body 114 draws the reference sample 112 into the tips 230 by suction from the microplate 102. The suction rate at this time is set to a rate preset in a computer for control and analysis which is not depicted.

(8) The detection optical system 119 is slid to the front side from the main body 114. Then, from a light source (not depicted) incorporated in the main body 114, test light is introduced into the pipette adapters 20 by way of optical fibers 123. The test light is bend by unshown reflecting mirrors within the pipette adapters 20 so as to be introduced into the tips 230.

(9) The detection optical system 119 detects the test light transmitted through the reference sample 112 contained in the tips 230.

(10) After the measurement of the reference sample 112 is completed, the detection optical system 119 is slid to the back side (toward the main body 114) so as to be returned to its initial position.

(11) The reference sample 112 within the tip 230 is dropped onto a microplate 113b provided on the X-stage 103, so as to be completely let out. The dropping rate at this time is a rate preset in the computer for control and analysis.

(12) Then, as with the reference sample 112, the sample 9 in the microplate 102a is drawn into the tips 230 by suction (at a suction rate identical to that in the case of the reference sample 112), and the test light is detected. After the completion of the measurement, the sample 9 within the tips 230 is dropped onto a microplate 113 provided on the X-stage 103, so as to be completely let out. The dropping rate at this time is set identical to that in the case of the reference sample 112.

The foregoing series of operations can automatically be carried out by the computer for control and analysis according to a predetermined sequence. As a consequence, a number of samples can be processed rapidly in a continuous or batch fashion, whereby the efficiency in absorbance measurement can be enhanced remarkably. Also, since the pipette adapters 20 and tips 230 in accordance with the present invention are employed, rapid measurement with a high accuracy and high precision and high reproducibility is possible for a minute amount of sample.

EXAMPLES

In the following, the present invention will be explained specifically with reference to Examples, which do not restrict the present invention as long as the latter does not exceed the gist thereof.

Example 1

Using a pipette adapter 20, configured as shown in FIG. 2, having a test light introducing window 23 made of synthetic quartz glass and a reflecting mirror 24 as a pipette adapter, and an absorbance measuring apparatus 100 configured as shown in FIG. 3 as an absorbance measuring apparatus, the absorbance of a sample was measured.

As other constituents, the following were used:

1) Tip 30: a general purpose product for 1000 μl
2) Pipette 10: Pipetman manufactured by Gilson, Inc.
3) Light source 40: a deuterium lamp (model: C6311-50) manufactured by Hamamatsu Photonics K.K.
4) Shutter 45: an electronic shutter manufactured by Copal Co., Ltd.
5) Band-pass filter 52: one selected from an interference filter having a maximum transmission wavelength of 260 nm manufactured by Melles Griot and an interference filter having a maximum transmission wavelength of 320 nm manufactured by Asahi Spectra Co., Ltd.
6) Photodetector 60: a photomultiplier (model: R1527HA; detectable wavelength range: 185 nm to 650 nm) manufactured by Hamamatsu Photonics K.K.
7) Ammeter 70: (model R8240) manufactured by Advantest Corp.

Before measuring the absorbance of the sample, the absorbance of distilled water alone, as a blank sample, was measured. First, the tip 30 is attached to the absorbance measuring pipette 1, and 200 μl of distilled water were metered into the tip 30. Then, while this state was maintained, the absorbance measuring pipette 1 was attached to the absorbance measuring apparatus 100 at a predetermined position thereof.

Subsequently, as the band-pass filter 52, one having a maximum transmission wavelength of 260 nm was set, and the shutter 45 was opened. Of the test light transmitted through distilled water in the tip 30, the 260 nm wavelength component was detected by the photodetector 60, its current value $I_{w260}$ was read out by the ammeter 70, and thus read-out value was stored in the computer 80. Then, the shutter 45 was closed. In the case where the absolute quantity of light is so small that the dark current of the photodetector 60 cannot be neglected, then it is necessary to measure the dark current while the shutter 45 is closed, and subtract the dark current value from the current value obtained when the test light is measured.

Subsequently, as the band-pass filter 52, one having a maximum transmission wavelength of 320 nm was set, and the shutter 45 was opened. Of the test light transmitted through distilled water in the tip 30, the 320 nm wavelength component was detected by the photodetector 60, its current value $I_{w320}$ was read out by the ammeter 70, and thus read-out value was stored in the computer 80. Then, the shutter 45 was closed.

Next, the absorbance of a sample 9 was measured. Employed as the sample 9 was a solution in which a nucleic acid (base sequence: AGCGCGCAATTAACCC) as a specimen had been dissolved as a solute in distilled water acting as a solvent. First, the tip 30 is attached to the absorbance measuring pipette 1, and 200 μl of the sample were metered into the tip 30 from a sample container. Then, while this state was maintained, the absorbance measuring pipette 1 was attached to the absorbance measuring apparatus 100 at a predetermined position thereof.

Subsequently, as the band-pass filter 52, one having a maximum transmission wavelength of 260 nm was set, and the shutter 45 was opened. Of the test light transmitted through the sample in the tip 30, the 260 nm wavelength component was detected by the photodetector 60, its current value $I^{d260}$ was read out by the ammeter 70, and thus read-out value was stored in the computer 80. Then, the shutter 45 was closed.

Subsequently, as the band-pass filter 52, one having a maximum transmission wavelength of 320 nm was set, and the shutter 45 was opened. Of the test light transmitted through the sample in the tip 30, the 320 nm wavelength component was detected by the photodetector 60, its current value $I_{d320}$ was read out by the ammeter 70, and thus read-out value was stored in the computer 80. Then, the shutter 45 was closed.

Thereafter, the absorbance of the sample 9 was determined according to the following procedure. A correction coefficient K in the solvent (distilled water) was determined according to the relationship represented by the following expression (1):

$$K = I_{w260}/I_{w320} \tag{1}$$

and absorbance A was determined according to the relationship represented by the following expression (2):

$$A = -\log_{10}(I_{d260}/I_{d320}/K) \tag{2}$$

As a consequence, the absorbance A of the sample 9 was 0.339. Also, the optical path length L in the sample within the tip 30 was measured, and the following expression (3):

$$L = 1.85 \text{ cm} \tag{3}$$

was obtained. Consequently, the absorbance Ac per 1 cm of optical path length was a value given by the following expression (4):

$$Ac = 0.339/L = 0.183 \tag{4}$$

Example 2

Using the absorbance measuring apparatus 200 configured as shown in FIGS. 7 and 8 in place of the absorbance measuring apparatus 100, and the tip 230 shown in FIG. 9 in place of the tip 30, the absorbance of the same sample 9 was measured 10 times as in Example 1. The band-pass filters of the filter disk 59 were the two kinds of band-pass filters used in Example 1. As a result, the average value of absorbance Ac of the sample 9 was 0.182, and its ratio of fluctuation was within the range of ±4.8% with respect to this average value.

Referential Example

For cross-checking the absorbance of the sample 9 obtained by Examples, the absorbance of the same sample 9 was measured with a Beckman spectrophotometer (model: DU-7500), whereby the absorbance per 1 cm of optical path length was 0.187. The difference between this value and the absorbance obtained in Example 1 was 0.004 (about 2%), whereby it was verified that the absorbance of the sample can accurately be measured with the absorbance measuring apparatus of the present invention.

In the present invention, as explained in detail in the foregoing, a pipette adapter is attached between a pipette and a tip, test light is introduced into the inner space of the pipette adapter, and this test light is emitted toward a sample suction port of the tip, whereby the absorbance of a sample in the tip is measured. Namely, without transferring the sample to a cell, the absorbance of the sample can be measured while the sample is in a state metered in the tip. Therefore, the step of recovering the sample can be omitted, the sample is prevented from being contaminated upon recovery, and it is not necessary to use a specific cell for absorbance measurement, whereby the absorbance of a minute amount of sample can be measured rapidly. Also, the measurement is inexpensive since conventional commercially available tips can be used, and the tips can be discarded after their use.

What is claimed is:

1. A pipette adapter usable together with a pipette for measuring an absorbance of a sample including a specimen, said pipette adapter being attachable between the pipette and a tip for containing a sample, having an inner space continuing to respective internal spaces of the pipette and tip when attached to said pipette adapter, and comprising test light introducing means for introducing light into the inner space from outside and emitting the test light toward a sample suction port of the tip.

2. The pipette adapter according to claim 1, wherein said test light introducing means comprises:
    a test light introducing window for introducing the test light into the inner space from outside; and
    a reflecting mirror for reflecting toward the sample suction port of the tip the test light introduced into the inner space through said test light introducing window.

3. The pipette adapter according to claim 1, wherein said test light introducing means comprises an optical fiber which emits, from a first end disposed within the inner space, toward the sample suction port of the tip, the test light guided through said optical fiber from outside.

4. The pipette adapter according to claim 3, further comprising test light collecting means disposed near said first end of said optical fiber, for collecting the test light.

5. The pipette adapter according to claim 1, wherein said test light introducing means selectively emits toward the sample suction port of the tip only a wavelength band component of the test light introduced into the inner space from outside.

6. An absorbance measuring pipette comprising a pipette adapter according to claim 1, and a pipette attachable to said pipette adapter.

7. The pipette adapter according to claim 6, further comprising a tip having an inserting portion, with a substantially conical or pyramidal form, for receiving said pipette adapter, and a sample container portion, in a tubular form, having an end part including a sample suction port.

8. An absorbance measuring apparatus for measuring an absorbance of a sample including a specimen, said apparatus comprising:
    a light source for outputting test light;
    an absorbance measuring pipette according to claim 6, introducing the test light output from said light source into the inner space of said tip, and emitting the test light toward the sample suction port of said tip; and
    a detection optical system for detecting the test light output from the sample suction port of said tip.

9. The absorbance measuring apparatus according to claim 8, further comprising arithmetic means for computing the absorbance of a sample in said tip according to an intensity of test light detected by said detection optical system when the sample is contained in said tip and an intensity of the test light detected by said detection optical system when no sample is contained in said tip or a blank sample including no specimen is contained in said tip.

10. The absorbance measuring apparatus according to claim 8, wherein said detection optical system simultaneously or substantially simultaneously detects intensities of a plurality of components having wavelengths different from each other of the test light output from the sample suction port of said tip.

11. The absorbance measuring apparatus according to claim 8, further comprising temperature adjusting means for cooling said tip or maintaining said tip at a constant temperature.

12. The absorbance measuring apparatus according to claim 8, wherein said pipette adapter has a side wall at least a part of which is conical or pyramidal, said apparatus further comprising means having a bore in which a part of the side wall of said pipette adapter having a conical or pyramidal form fits.

13. An absorbance measuring method for measuring an absorbance of a sample including a specimen, said method comprising:
    attaching a tip for containing a sample to the absorbance measuring pipette according to claim 6;
    placing in said tip a sample or a blank sample including no specimen;
    introducing test light into the inner space of said absorbance measuring pipette from outside and detecting the test light output from the sample suction port of said tip; and
    calculating the absorbance of a sample contained in said tip according to intensity of the test light detected when the sample is contained in said tip and intensity of the test light detected when no sample is contained in said tip or when a blank sample is contained in said tip.

14. The absorbance measuring method according to claim 13, wherein intensities of a plurality of components having wavelengths different from each other in the test light output from the sample suction port of said tip are detected simultaneously or substantially simultaneously in detecting the test light.

15. The absorbance measuring method according to claim 13, including detecting the test light while said tip is cooled or maintained at a constant temperature.

16. A tip attachable to the pipette adapter according to claim 1, said tip having a sample container portion for containing a sample including a specimen, said sample container portion having a tubular form and substantially parallel inner walls in a cross section taken along a center axis.

17. A tip attachable to the pipette adapter according to claim 1, said tip including a light-shielding member for substantially blocking test light irradiating a sample including a specimen.

* * * * *